UNITED STATES PATENT OFFICE.

SAMUEL A. FORD, OF PITTSBURG, PENNSYLVANIA.

PROCESS OF ANALYZING PIG-IRON FROM BLAST-FURNACES.

SPECIFICATION forming part of Reissue Letters Patent No. 10,395, dated October 23, 1883.

Original patent No. 281,044, dated July 10, 1883. Application filed September 6, 1883.

*To all whom it may concern:*

Be it known that I, SAMUEL A. FORD, of Pittsburg, in the county of Allegheny and State of Pennsylvania, have invented certain new and useful Improvements in Processes of Analyzing Pig-Iron from Blast-Furnaces; and I do hereby declare that the following is a full, clear, and exact description of the invention, that will enable others skilled in the art to which it appertains to make and use the same.

In the manufacture of steel, whether Bessemer or open hearth, by the "direct process," wherein the molten metal is taken directly from the blast-furnace to the converter or furnace, it is practically out of the question to obtain a running analysis of the charge in time to be of service. If the usual "sample" be cast and allowed to cool in the ordinary way, the analysis cannot be had for several hours. If the sample-piece be suddenly cooled in water, it chills, and cannot be readily broken up or drilled for the test. Meanwhile the ladle of molten metal drawn from the blast-furnace cannot be held for such a length of time; hence the character of the contents of the ladle must be, to a certain extent, guessed at, especially with reference to the contained silicon. My object is to make an immediate test practicable without delaying the transfer of the metal from the blast-furnace.

The invention consists, briefly, in taking a small quantity of the molten iron and granulating it in such manner that it will be brittle, and then crushing and analyzing the granules. More fully, my invention is as follows: Usually the metal is transferred in a ladle set on trucks, and as the converting-works are generally some distance from the blast-furnace, it generally takes from twenty minutes to a half-hour from the first tapping of the blast-furnace till the ladle is brought to the converter. As soon as the metal begins to run from the furnace I catch or dip up a small quantity of it and cause it to form into brittle granules. One way to granulate the iron is to let it drop several feet into water, preferable clean water in a clean vessel. As soon as it strikes the water the metal divides into small globules or pellets, which chill at once. These can be taken at once to the laboratory, and, being extremely brittle, they can be very readily crushed in a steel mortar, and thus reduced to the condition required for analysis. As the analysis, which is at this stage desired, requires but a few minutes to determine, the result is that I can have the report on the contents of the ladle ready by the time the latter has arrived at the converting-works. There is therefore no delay caused in the proper carrying out of the direct process, and at the same time the precise character of the metal being analytically determined, the reagents of conversion may be accurately regulated and the standard product maintained, a result which is unattainable in the present practice of making samples and boring them after slow cooling.

I claim as my invention—

1. The method of analyzing the runs of a blast-furnace, consisting in first granulating some of the molten metal to a brittle condition and then crushing and analyzing the said granules, substantially as described.

2. The method of analyzing the runs of a blast-furnace, consisting in first granulating some of the molten metal by pouring into water and then crushing and analyzing the said granules, substantially as described.

In testimony that I claim the foregoing I have hereunto set my hand.

SAMUEL A. FORD.

Witnesses:

THOS. J. MCTIGHE,

THOMAS J. PATTERSON.